(12) United States Patent
Peker et al.

(10) Patent No.: US 8,002,911 B2
(45) Date of Patent: *Aug. 23, 2011

(54) METALLIC DENTAL PROSTHESES AND OBJECTS MADE OF BULK-SOLIDIFYING AMORPHHOUS ALLOYS AND METHOD OF MAKING SUCH ARTICLES

(75) Inventors: Atakan Peker, Aliso Viejo, CA (US); Choongnyun Paul Kim, Northridge, CA (US); Tranquoc ThebaoNguyen, Anaheim, CA (US)

(73) Assignee: Crucible Intellectual Property, LLC, Rancho Santa Margarita, CA (US)

( * ) Notice: Subject to any disclaimer, the term of this patent is extended or adjusted under 35 U.S.C. 154(b) by 352 days.

This patent is subject to a terminal disclaimer.

(21) Appl. No.: 10/523,465

(22) PCT Filed: Aug. 5, 2003

(86) PCT No.: PCT/US03/24461
§ 371 (c)(1),
(2), (4) Date: Nov. 15, 2005

(87) PCT Pub. No.: WO2004/012620
PCT Pub. Date: Feb. 12, 2004

(65) Prior Publication Data
US 2006/0108033 A1    May 25, 2006

Related U.S. Application Data

(60) Provisional application No. 60/401,303, filed on Aug. 5, 2002.

(51) Int. Cl.
*C22C 45/02* (2006.01)
(52) U.S. Cl. ........... 148/403; 148/337; 420/94; 420/125
(58) Field of Classification Search .................. 148/403
See application file for complete search history.

(56) References Cited

U.S. PATENT DOCUMENTS

| | | | |
|---|---|---|---|
| 2,106,145 A | 1/1938 | Floraday | |
| 2,124,538 A | 7/1938 | Boyer | |
| 3,322,546 A | 5/1967 | Tanzman et al. | |
| 3,539,192 A | 11/1970 | Prasse | |
| 3,776,297 A | 12/1973 | Williford et al. | |
| 3,948,613 A | 4/1976 | Weill | |
| 3,970,445 A | 7/1976 | Gale et al. | |
| 3,986,867 A | 10/1976 | Masumoto et al. | |
| 3,986,892 A | 10/1976 | Eve et al. | |
| 3,989,517 A | 11/1976 | Tanner et al. | |
| 4,024,902 A | 5/1977 | Baum | |
| 4,050,931 A | 9/1977 | Tanner et al. | |
| 4,064,757 A | 12/1977 | Hasegawa | |
| 4,067,732 A | 1/1978 | Ray | |
| 4,113,478 A | 9/1978 | Tanner et al. | |
| 4,116,682 A | 9/1978 | Polk et al. | |
| 4,116,687 A | 9/1978 | Hasegawa | |
| 4,124,472 A | 11/1978 | Riegert | |
| 4,125,737 A | 11/1978 | Andersson | |
| 4,126,449 A | 11/1978 | Tanner et al. | |
| 4,135,924 A | 1/1979 | Tanner et al. | |
| 4,148,669 A | 4/1979 | Tanner et al. | |
| 4,157,327 A | 6/1979 | Martin et al. | |
| 4,163,071 A | 7/1979 | Weatherly et al. | |
| 4,260,416 A | 4/1981 | Kavesh et al. | |
| 4,268,564 A | 5/1981 | Narasimhan | |
| 4,330,027 A | 5/1982 | Narasimhan | |
| 4,374,900 A | 2/1983 | Hara et al. | |
| 4,381,943 A | 5/1983 | Dickson et al. | |
| 4,396,820 A | 8/1983 | Puschner | |
| 4,409,296 A | 10/1983 | Ward | |
| 4,478,918 A | 10/1984 | Ueno et al. | |
| 4,482,612 A | 11/1984 | Kuroki et al. | |
| 4,487,630 A | 12/1984 | Crook et al. | |
| 4,488,882 A | 12/1984 | Dausinger et al. | |
| 4,499,158 A | 2/1985 | Onuma et al. | |
| 4,515,870 A | 5/1985 | Bose et al. | |
| 4,523,625 A | 6/1985 | Ast | |
| 4,526,618 A | 7/1985 | Keshavan et al. | |
| 4,557,981 A | 12/1985 | Bergmann | |
| 4,564,396 A | 1/1986 | Johnson et al. | |
| 4,585,617 A | 4/1986 | Tenhover et al. | |
| 4,612,059 A | 9/1986 | Mori et al. | |
| 4,623,387 A | 11/1986 | Masumoto et al. | |
| 4,648,609 A | 3/1987 | Deike | |
| 4,656,099 A | 4/1987 | Sievers | |

(Continued)

FOREIGN PATENT DOCUMENTS
DE         010237992 A1     3/2003
(Continued)

OTHER PUBLICATIONS

Inoue, A., et al., Bulk Amorphous Alloys with High Mechanical Strength and Good Soft Magnetic Properties in Fe-TM-B (TM=IV-VIII Group transition Metal) System, Appl. Phys. Lett., vol. 71, No. 4, Jul. 28, 1997, pp. 464-466.*

(Continued)

*Primary Examiner* — George Wyszomierski
(74) *Attorney, Agent, or Firm* — Pillsbury Winthrop Shaw Pittman LLP

(57) ABSTRACT

Metallic dental prostheses made of bulk-solidifying amorphous alloys wherein the dental prosthesis has an elastic strain limit of around 1.2% or more and methods of making such metallic dental prostheses are provided.

26 Claims, 1 Drawing Sheet

U.S. PATENT DOCUMENTS

| | | | |
|---|---|---|---|
| 4,668,310 A | 5/1987 | Kudo et al. |
| 4,721,154 A | 1/1988 | Christ et al. |
| 4,725,512 A | 2/1988 | Scruggs |
| 4,731,253 A | 3/1988 | DuBois |
| 4,741,974 A | 5/1988 | Longo et al. |
| 4,743,513 A | 5/1988 | Scruggs |
| 4,770,701 A | 9/1988 | Henderson et al. |
| 4,810,850 A | 3/1989 | Tenkula et al. |
| 4,960,643 A | 10/1990 | Lemelson |
| 4,976,417 A | 12/1990 | Smith |
| 4,978,590 A | 12/1990 | Granata, Jr. et al. |
| 4,987,033 A | 1/1991 | Abkowitz et al. |
| 4,990,198 A | 2/1991 | Masumoto et al. |
| 5,032,196 A | 7/1991 | Masumoto et al. |
| 5,053,084 A | 10/1991 | Masumoto et al. |
| 5,053,085 A | 10/1991 | Masumoto et al. |
| 5,127,969 A | 7/1992 | Sekhar |
| 5,189,252 A | 2/1993 | Huffman et al. |
| 5,213,148 A | 5/1993 | Masumoto et al. |
| 5,250,124 A | 10/1993 | Yamaguchi et al. |
| 5,279,349 A | 1/1994 | Horimura |
| 5,288,344 A | 2/1994 | Peker et al. |
| 5,294,462 A | 3/1994 | Kaiser et al. |
| 5,302,471 A | 4/1994 | Ito et al. |
| 5,324,368 A | 6/1994 | Masumoto et al. |
| 5,368,659 A | 11/1994 | Peker et al. |
| 5,380,349 A | 1/1995 | Taniguchi et al. |
| 5,380,375 A | 1/1995 | Hashimoto et al. |
| 5,384,203 A | 1/1995 | Apfel |
| 5,440,995 A | 8/1995 | Levitt |
| 5,449,425 A | 9/1995 | Renard et al. |
| 5,482,577 A | 1/1996 | Hashimoto et al. |
| 5,482,580 A | 1/1996 | Scruggs et al. |
| 5,567,251 A | 10/1996 | Peker et al. |
| 5,567,532 A | 10/1996 | Peter et al. |
| 5,618,359 A * | 4/1997 | Lin et al. | 148/561 |
| 5,634,989 A | 6/1997 | Hashimoto et al. |
| 5,711,363 A | 1/1998 | Scruggs et al. |
| 5,735,975 A | 4/1998 | Lin et al. |
| 5,797,443 A | 8/1998 | Lin et al. |
| 5,886,254 A | 3/1999 | Chi |
| 5,950,704 A | 9/1999 | Johnson et al. |
| 6,010,580 A | 1/2000 | Dandliker et al. |
| 6,021,840 A | 2/2000 | Colvin |
| 6,027,586 A | 2/2000 | Masumoto et al. |
| 6,044,893 A | 4/2000 | Taniguchi et al. |
| 6,066,176 A * | 5/2000 | Oshida | 623/23.62 |
| 6,183,889 B1 | 2/2001 | Koshiba et al. |
| 6,200,685 B1 | 3/2001 | Davidson |
| 6,203,936 B1 | 3/2001 | Cisar et al. |
| 6,218,029 B1 | 4/2001 | Rickerby |
| 6,258,183 B1 | 7/2001 | Onuki et al. |
| 6,306,206 B1 * | 10/2001 | Fischer et al. | 106/35 |
| 6,306,228 B1 | 10/2001 | Inoue et al. |
| 6,325,868 B1 | 12/2001 | Kim et al. |
| 6,326,295 B1 | 12/2001 | Figura |
| 6,371,195 B1 | 4/2002 | Onuki et al. |
| 6,376,091 B1 | 4/2002 | Croopnick |
| 6,408,734 B1 | 6/2002 | Cohen |
| 6,446,558 B1 | 9/2002 | Peker et al. |
| 6,749,698 B2 * | 6/2004 | Shimizu et al. | 148/403 |
| 2001/0052406 A1 | 12/2001 | Kubota et al. |
| 2002/0036034 A1 | 3/2002 | Xing et al. |
| 2002/0050310 A1 | 5/2002 | Kundig et al. |
| 2002/0162605 A1* | 11/2002 | Horton et al. | 148/304 |
| 2002/0187379 A1 | 12/2002 | Yasuo et al. |

FOREIGN PATENT DOCUMENTS

| | | |
|---|---|---|
| GB | 2005302 | 4/1979 |
| JP | 55-14090 | 9/1981 |
| JP | 359013056 A | 1/1984 |
| JP | 05-051965 | 9/1994 |
| JP | 11-066094 | 9/2000 |
| JP | 02000277127 A | 10/2000 |
| JP | 02001303218 A | 10/2001 |
| WO | WO00/68469 A2 | 11/2000 |
| WO | WO03/040422 A1 | 5/2003 |

OTHER PUBLICATIONS

Author unknown, "Standard Practice for Conducting Dry Sand/Rubber Wheel Abrasion Tests", Designation G 65-81, source unknown, pp. 351-368, Dec. 1981.

Koch et al., "Preparation of "Amorphous" $Ni_{60}Nb_{40}$ By Mechanical Alloying", Appl. Phys. Lett., Dec. 1983, vol. 43, No. 11, pp. 1017-1019.

Author unknown, "A World of Superabrasives Experience At Your Service", source unknown, 4 pgs.

Author unknown, "GE Superabrasives—The Metal Bond System", source unknown, 1 page.

Author unknown, "GE Superabrasives—The Resin Bond System", source unknown, 1 page.

Author unknown, "GE Superabrasives—Micron Powders", source unknown, 1 page.

Author unknown, "GE Superabrasives—The MBS 700 Series Product Line", source unknown, 2 pages, 1991.

Author unknown, "GE Superabrasives—The MBS-900 Series Product Line", source unknown, 2 pages, 1992.

Masumoto, "Recent Progress in Amorphous Metallic Materials in Japan", Materials Science and Engineering, 1994, vol. A179/A180, pp. 8-16.

ASM Committee on Tooling Materials, "Superhard Tool Materials", Metals Handbook, Ninth Edition, vol. 3, Properties and Selection: Stainless Steels, Tool Materials and Special Purpose Metals, American Society for Metals, 1980, pp. 448-465, title page and copyright page.

Zhang et al., "Amoprphous Zr-Al-TM (TM=Co, Ni, Cu) Alloys with Significant Supercooled Liquid Region of Over 100K", Materials Transactions, JIM, 1991, vol. 32, No. 11, pp. 1005-1010.

Inoue et al., "Zr-Al-Ni Amorphous Alloys with High Glass Transition Temperature and Significant Supercooled Liquid Region", Materials Transactions, JIM, 1990, vol. 31, No. 3, pp. 177-183.

Tanner et al., "Physical Properties of $Ti_{50}Be_{40}Zr_{10}$ Glass", Scripta Metallurgica, 1977, vol. 11, pp. 783-789.

Tanner, L.E., "Physical Properties of Ti-Be-Si Glass Ribbons", Scripta Metallurgica, 1978, vol. 12, pp. 703-708.

Hasegawa et al., "Superconducting Properties of Be-Zr Glassy Alloys Obtained by Liquid Quenching", May 9, 1977, pp. 3925-3928.

Tanner, L.E., "The Stable and Metastable Phase Relations in the Hf-Be Alloy System", Metallurgica, vol. 28, 1980, pp. 1805-1815.

Maret et al., "Structural Study of $Be_{43}Hf_xZr_{57-x}$ Metallic Glasses by X-Ray and Neutron Diffraction", J. Physique, 1986, vol. 47, pp. 863-871.

Jost et al., "The Structure of Amorphous Be-Ti-Zr Alloys", Zeitschrift fur Physikalische Chemie Neue Folge, Bd. 157, 1988, pp. 11-15.

Tanner et al., "Metallic Glass Formation and Properties in Zr and Ti Alloyed with Be-I The Binary Zr-Be and Ti-Be Systems", Acta Metallurgica, 1979, vol. 27, pp. 1727-1747.

\* cited by examiner

US 8,002,911 B2

METALLIC DENTAL PROSTHESES AND OBJECTS MADE OF BULK-SOLIDIFYING AMORPHHOUS ALLOYS AND METHOD OF MAKING SUCH ARTICLES

CROSS-REFERENCE TO RELATED APPLICATIONS

This application is a National Stage of International Application No. PCT/US2003/024461, filed Aug. 5, 2003, which claims the benefit of U.S. Provisional Application No. 60/401,303, filed Aug. 5, 2002.

FIELD OF THE INVENTION

The present invention relates to metallic dental prostheses constructed of bulk-solidifying amorphous alloys and methods of making such articles.

BACKGROUND OF THE INVENTION

Metallic dental prostheses, such as crown and bridges, are each custom-made to replicate the impressions made for a specific tooth/teeth. Generally, metallic dental prostheses are made from various metals and alloys using an investment casting process. The materials are chosen for their ability to replicate the exact features of the impression during casting, and the ability to attain a high quality surface finish during the post-cast finishing process. In addition, the choice of dental material should have a high yield strength and sufficient hardness to endure the stresses created by chewing, and sufficient erosion/corrosion resistance to withstand the harsh chemical environment created by various foods, by the body, and by the environment. Finally, the material of choice should have a relatively low coefficient of thermal expansion to be compatible with the tooth and other porcelain materials it is place in contact with.

The principal materials of choice for metallic dental prostheses are noble-metal based alloys, such as gold alloys, which are corrosion resistant and have better relative castability than conventional high strength materials. However, these noble-metal based alloys are expensive materials and generally do no have high yield strength and hardness. Other materials of choice, such as nickel-base alloys, are difficult to cast and do not sufficiently replicate the exact features of the intricate impressions.

Accordingly, there is a need for a new material for metallic dental prostheses, with high castability and replication characteristics, high yield strength and hardness, high corrosion resistance, and that are preferably relatively inexpensive.

SUMMARY OF THE INVENTION

The current invention is directed to metallic dental prostheses made of bulk-solidifying amorphous alloys wherein the dental prosthesis has an elastic strain limit of around 1.8% or more, and methods of making such metallic dental prostheses.

In one embodiment of the invention, the metallic dental prosthesis is made of a bulk-solidifying amorphous alloy. In one preferred embodiment of the invention, the metallic dental prosthesis is made of a Zr/Ti base bulk-solidifying amorphous alloy incorporating in-situ ductile crystalline precipitates.

In another preferred embodiment of the invention, the metallic dental prosthesis is made of a Zr/Ti base bulk-solidifying amorphous alloy incorporating no Nickel.

In still another preferred embodiment of the invention, the metallic dental prosthesis is made of a Zr/Ti base bulk-solidifying amorphous alloy incorporating no Aluminum.

In yet another preferred embodiment of the invention, the metallic dental prosthesis is made of a Zr/Ti base bulk-solidifying amorphous alloy incorporating no Beryllium.

In another embodiment of the invention, the metallic dental prostheses are comprised at least in part of another dental material.

In still another embodiment of the invention, the metallic dental prosthesis is coated with a biocompatible polymethyl methacrylate resin cement. In such an embodiment the cement can be reinforced with selected oxides including alumina, magnesia, zirconia, or a combination of these oxides along with an application of a small amount of a metal primer agent.

In yet another embodiment of the invention, the metallic dental prosthesis is a casting of a bulk-solidifying amorphous alloy. In a preferred embodiment of the invention, metallic dental prosthesis is an investment casting of a bulk-solidifying amorphous alloy.

In still yet another embodiment of the invention, the metallic dental prosthesis is a crown. In another embodiment of the invention, the metallic dental prosthesis is a bridge.

In still yet another embodiment the invention is directed to a method of forming a dental prosthesis of a bulk-solidifying alloy. In one such embodiment, a molten piece of bulk-solidifying amorphous alloy is cast into a near-to-net shape dental prostheses. In a preferred embodiment of the invention a molten piece of bulk-solidifying amorphous alloy is investment-cast into a near-to-net shape dental prostheses. In another preferred embodiment of the invention, a molten piece of bulk-solidifying amorphous alloy is cast into a near-to-net shape crown. In still another preferred embodiment of the invention, a molten piece of bulk-solidifying amorphous alloy is investment-cast into a near-to-net shape crown. In yet another preferred embodiment of the invention, a molten piece of bulk-solidifying amorphous alloy is cast into a near-to-net shape bridge. In still yet another preferred embodiment of the invention, a molten piece of bulk-solidifying amorphous alloy is investment-cast into a near-to-net shape bridge.

In another embodiment of the method of making dental prostheses, the bulk solidifying amorphous alloy composition has a critical cooling rate of 100° C./second or less and preferably 10° C./second or less.

In still another embodiment of the method of making dental prostheses, the provided bulk solidifying amorphous alloy composition is selected from the group consisting of: Zr/Ti base, Zr-base, Zr/Ti base with no Ni, Zr/Ti base with no Al, and Zr/Ti base with no Be.

In yet another embodiment of the method of making dental prostheses, a molten piece of the bulk-solidifying amorphous alloy is cast into a dental prosthesis under either a partial vacuum or a vacuum.

In still yet another embodiment of the method of making dental prostheses, a molten piece of the bulk-solidifying amorphous alloy is fed into the mold by applying an external pressure such as an inert gas.

BRIEF DESCRIPTION OF THE DRAWINGS

These and other features and advantages of the present invention will be better understood by reference to the following detailed description when considered in conjunction with the accompanying drawing wherein.

DETAILED DESCRIPTION OF THE INVENTION

Figure 1:
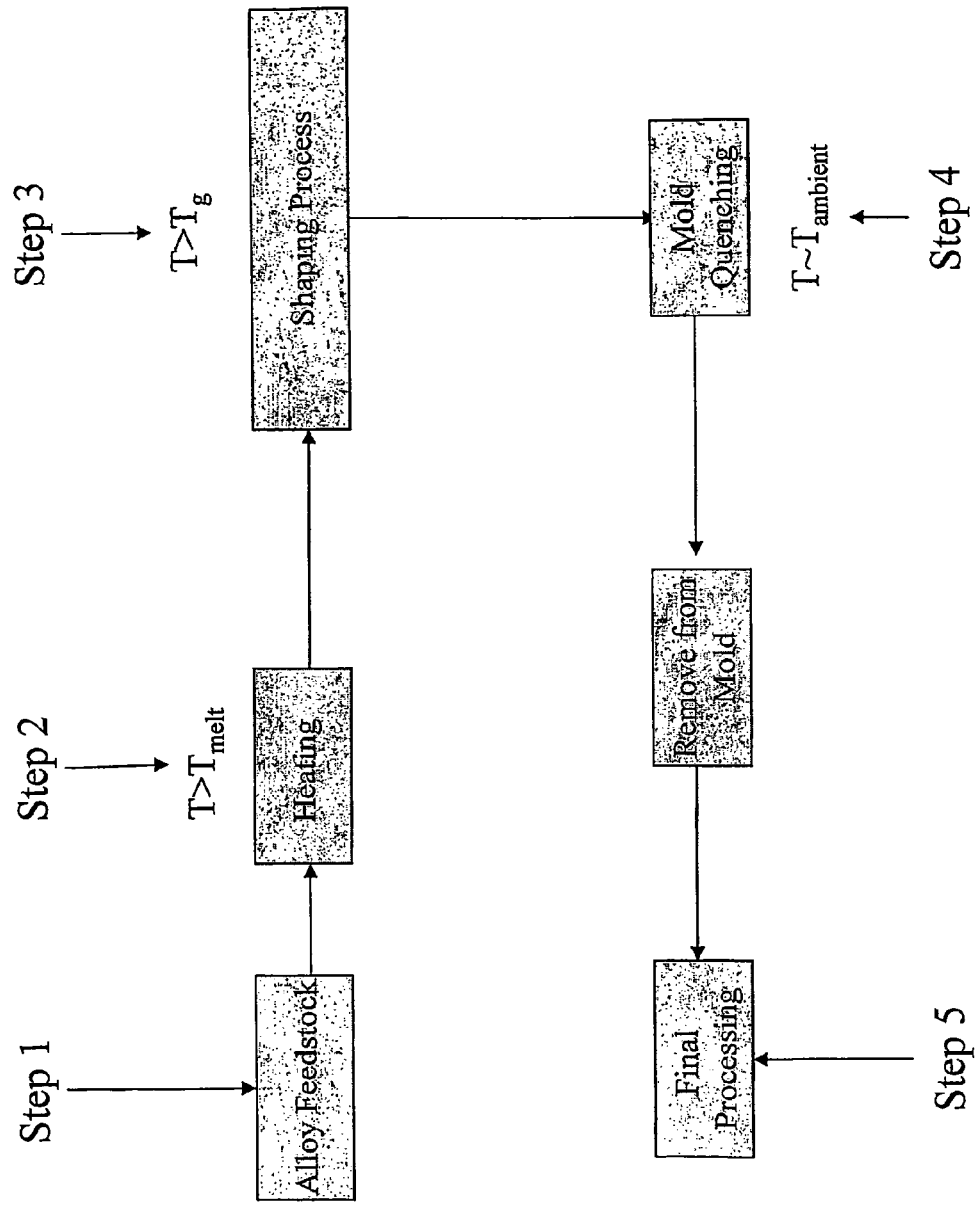
FIG. 1 shows a flow-chart an exemplary embodiment of a method of producing a metallic dental prosthesis according to the current invention.

The current invention is directed to metallic dental prostheses made of bulk-solidifying amorphous alloys wherein the dental prosthesis has an elastic strain limit of around 1.8% or more, and methods of making such metallic dental prostheses.

Metallic dental prostheses, such as crowns and bridges, are each custom-made to replicate the impressions made for a specific tooth/teeth. In dental terminology, the crown is the visible part of tooth, which can be further covered by enamel to improve the aesthetics and durability of the prosthesis. Such a crown can be an artificial replacement for the visible part of a tooth that has decayed or been damaged. In such an embodiment, the crown is a restoration that covers, or caps, a tooth to restore it to its normal shape and size. However, the crown can also serve to strengthen or improve the appearance of a tooth. Finally, the crown can also be used to cover a dental implant.

In contrast, a bridge is a partial false tooth, or a set of one or more false teeth that act as a replacement for missing natural teeth. Such a bridge can be permanently anchored to natural teeth (fixed bridge) or set into a metal appliance and temporarily clipped onto natural teeth (removable bridge).

Bulk solidifying amorphous alloys are recently discovered family of amorphous alloys, which can be cooled at substantially lower cooling rates, of about 500 K/sec or less, and substantially retain their amorphous atomic structure. As such, these materials can be produced in thickness of 1.0 mm or more, substantially thicker than conventional amorphous alloys, which have typical thicknesses of 0.020 mm, and which require cooling rates of $10^5$ K/sec or more. Exemplary bulk-solidifying amorphous alloy materials are described in U.S. Pat. Nos. 5,288,344; 5,368,659; 5,618,359; and 5,735,975 (the disclosures of which are incorporated in their entirety herein by reference).

One exemplary family of bulk solidifying amorphous alloys can be described as $(Zr,Ti)_a(Ni,Cu, Fe)_b(Be,Al,Si,B)_c$, where a is in the range of from 30 to 75, b is in the range of from 5 to 60, and c in the range of from 0 to 50 in atomic percentages. Furthermore, these alloys can accommodate other transition metals, such as Nb, Cr, V, Co, in amounts up to 20% atomic and more.

A preferable alloy family is $(Zr,Ti)_a(Ni,Cu)_b(Be)_c$, where a is in the range of from 40 to 75, b is in the range of from 5 to 50, and c in the range of from 5 to 50 in atomic percentages. Still, a more preferable composition is $(Zr,Ti)_a(Ni,Cu)_b(Be)_c$, where a is in the range of from 45 to 65, b is in the range of from 7.5 to 35, and c in the range of from 10 to 37.5 in atomic percentages. Another preferable alloy family is $(Zr)_a(Nb,Ti)_b(Ni,Cu)_c(Al)_d$, where a is in the range of from 45 to 65, b is in the range of from 0 to 10, c is in the range of from 20 to 40 and d in the range of from 7.5 to 15 in atomic percentages. Other elements, e.g Y, Si, Sn, Sc etc. can also be added as microalloying additions to the composition of bulk solidifying amorphous alloys at fractions of atomic percentages in order to alleviate the effects of detrimental impurities such as oxygen and as such reduce the critical cooling rate.

These bulk-solidifying amorphous alloys can sustain strains up to 1.5% or more and generally around 1.8% without any permanent deformation or breakage. Further, they have high fracture toughness of 10 ksi-sqrt(in) (sqrt: square root) or more, and preferably 20 ksi sqrt(in) or more. Also, these materials have high hardness values of 4 GPa or more, and preferably 5.5 GPa or more. The yield strength of bulk solidifying alloys range from 1.6 GPa and reach up to 2 GPa and more exceeding the current state of the Titanium alloys.

Another set of bulk-solidifying amorphous alloys are ferrous metals (Fe, Ni, Co) based compositions. Examples of such compositions are disclosed in U.S. Pat. No. 6,325,868; publications to (A. Inoue et. al., Appl. Phys. Lett., Volume 71, p 464 (1997)) and (Shen et. al., Mater. Trans., JIM, Volume 42, p 2136 (2001)); and Japanese patent application 2000126277 (Publ. #.2001303218 A), all of which are incorporated herein by reference.

One exemplary composition of such alloys is $Fe_{72}Al_5Ga_2P_{11}C_6B_4$. Another exemplary composition of such alloys is $Fe_{72}Al_7Zr_{10}Mo_5W_2B_{15}$. Although, these alloy compositions are not processable to the degree of the above-cited Zr-base alloy systems, they can still be processed in thicknesses of around 1.0 mm or more, sufficient to be utilized in the current invention. Similarly, these materials have elastic strain limits higher than 1.2% and generally around 1.8%. The yield strength of these ferrous-based bulk-solidifying amorphous alloys is also higher than the Zr-based alloys, ranging from 2.5 GPa to 4 GPa, or more, making them particularly attractive for use in dental prostheses. Ferrous metal-base bulk amorphous alloys also very high yield hardness ranging from 7.5 GPA to 12 GPa.

In general, crystalline precipitates in bulk amorphous alloys are highly detrimental to the properties of bulk-solidifying amorphous alloys, especially to the toughness and strength of these materials, and, as such, such precipitates are generally kept to as small a volume fraction as possible. However, there are cases in which ductile crystalline phases precipitate in-situ during the processing of bulk amorphous alloys and are indeed beneficial to the properties of bulk amorphous alloys, and especially to the toughness and ductility of the materials. Such bulk amorphous alloys comprising such beneficial precipitates are also included in the current invention. One exemplary material is disclosed in (C. C. Hays et. al, Physical Review Letters, Vol. 84, p 2901, 2000), which is incorporated herein by reference. This alloy has a low elastic modulus of from 70 GPa to 80 GPa depending on the specific microstructure of ductile-crystalline precipitates. Further, the elastic strain limit is 1.8% or more and the yield strength is 1.4 GPa and more.

Although generally the current invention is directed to improved metallic dental prostheses, Applicants have found that dental prostheses constructed of bulk-solidifying amorphous alloys show a number of improved properties. First, as described above, bulk solidifying amorphous alloys have the high hardness and toughness properties associated with conventional materials. The bulk solidifying amorphous alloys also have excellent corrosion resistance, as required for any material exposed to the harsh conditions to which dental prostheses are subjected. However, these bulk-solidifying amorphous alloys also have some general characteristics which make bulk-solidifying amorphous alloys uniquely suited as a new class of material for the use and application in metallic dental prostheses.

Bulk-solidifying amorphous alloys have very high elastic strain limits, or the ability to sustain strains without permanent deformation, typically around 1.8% or higher. Although Applicant's have discovered that this is an important characteristic for dental prostheses because a high elastic limit helps to sustain global and local loading with minimal or no permanent deformation of the metallic dental prostheses, this characteristic is absent in conventional metallic dental materials. For example, conventional metals and alloys typically used in dental prostheses have typical elastic strain limits below 0.8%. Accordingly, dental prosthesis made of bulk-solidifying amorphous alloys having an elastic strain limit of 1.5% or higher, and preferably 1.8% or higher is desired.

The elastic limit of a material is also critical because metallic dental prostheses, such as the crowns and bridges discussed above, have highly intricate shapes and features, which must remain intact upon any mechanical loading both during preparation and in use. For example, because of the need to fit the crown and/or bridge as close to the tooth as possible, generally these prostheses have thin-walled shells as part of their overall shape and design. A material having a high elastic strain limit helps to keep both the general shape and intricate details of the metallic dental prostheses intact. In the case of conventional metals and alloys with much lower elastic strain limit, the use of thicker shells and larger structures are needed to sustain mechanical loading, as well as to maintain the integrity of the intricate details of the impression. Both thicker shells and larger structures are highly undesirable due to the increased operational and surgical complications. In addition, in some cases, these thicker shells and larger structures require that a larger section of the healthy tooth or teeth be cut away during operation in order to accommodate the crown or bridge in the patient.

Secondly, bulk solidifying amorphous alloys can be readily cast from the molten state to replicate the very details of impression prepared for dental prosthesis. Indeed, Applicants have discovered that the low melting temperatures of bulk-solidifying amorphous alloys provide a relatively easier casting operation such as reduced or minimal reaction with molds or investment shells. Further, the lack of any first-order phase transformation during the solidification of the bulk solidifying amorphous alloy reduces solidification shrinkage and as such provides a near-to-net shape configuration of the metallic dental prosthesis. The solidification shrinkage is then dominated by the coefficient of thermal expansion rather than the volume difference between the solid and liquid state of the casting alloy. Accordingly, bulk amorphous alloys with low coefficient thermal expansion (at temperatures from ambient to glass transition) are preferred. For example, Zr-base bulk solidifying amorphous alloys have generally a coefficient of thermal expansion of around $10^{-5}$ (m/m ° C.) providing low shrinkage rates. This is extremely important in the production of metallic dental prostheses since many of the intricate portions of the impressions can be lost if significant post-cast processing is required. In addition, bulk-solidifying amorphous alloys keep their fluidity to exceptionally low temperatures, such as down to the glass transition temperature, compared to other dental casting materials, and especially those materials which exhibit the necessary yield strengths for use in metallic dental prosthesis applications. Accordingly, bulk-solidifying amorphous alloys with glass transition temperatures lower than 400° C., and most preferably lower than 300° C. are preferred. For example, Zr—Ti base bulk-solidifying amorphous alloys have typical glass transition temperatures in the range of 320° C. to 450° C. depending on the alloy composition.

Applicants have discovered that these characteristics combined with the lack of any microstructure allow bulk-solidifying amorphous alloys to replicate the intricacies of the impressions in a dental casting with exceptional quality. The casting characteristics of bulk-solidifying amorphous alloys not only reduce the post-cast finishing processes, but also provide a better surface finish and preparation due to reduced or minimal defects arising from the initial casting operation. For example, a dental prosthesis constructed of a bulk-solidifying amorphous alloy can be given a very high polish and surface smoothness which helps to hinder bacteria growth in the mouth. Further, the high polish and other surface smoothness characteristics can be desirable from an aesthetic perspective as well.

While the above discussion has focussed primarily on the high elastic limit and castability properties of bulk-solidifying amorphous alloys, it should be understood that it is the unique combination of properties that makes these materials particularly suitable for use in metallic dental prostheses. For example the bulk-solidifying amorphous alloys described herein exhibit a very high hardness of 4.0 GPa or more leading to improved wear resistance, and inert properties which leads to improved corrosion resistance over conventional materials. For example, Zr-base bulk-solidifying amorphous alloys have hardness values ranging from 4.0 GPa up to 6.0 GPa. In addition, the yield strength of the bulk-solidifying amorphous alloys is exceptionally high, especially compared to the crystalline alloys of their base metals (e.g., Zr/Ti base amorphous alloys have typical yield strengths on the order of 1.5 to 2.0 GPa). Such properties, a hardness value of greater than 4.0 GPa and preferably more than 5.0 GPa, along with the very high elastic strain limit of 1.2%, preferably 1.5%, and most preferably 1.8% or higher, makes metallic dental prostheses of bulk-solidifying amorphous alloys highly durable. Moreover, because of the excellent castability of these materials the desired mechanical and physical properties of bulk-solidifying amorphous alloys are readily obtained in an as-cast condition. This is generally not true for conventional metals and alloys which are often not available at all as castings.

Although the above discussion has focussed solely on choosing a bulk-solidifying amorphous alloy material based on certain advantageous physical properties, the bulk solidifying amorphous alloy composition can also be preferably selected to be free of Ni or Al or Be in order to address the high sensitivity or allergic reactions of specific population groups to such metals.

The invention is also directed to a method of manufacturing the metallic dental prostheses of the invention. Principally the bulk-solidifying amorphous alloys are fabricated by various casting methods. For example, in one exemplary embodiment, as shown in FIG. 1, a feedstock of bulk solidifying amorphous alloy composition is provided (step 1). This feedstock does not to have to be in amorphous phase. Then in a second step (step 2) the feedstock alloy is heated into the molten state above the melting temperature of bulk-solidifying amorphous alloy. Then in a third step (step 3) the molten alloy is fed into the mold having the shape of the desired dental prosthesis. After, the complete fill of the mold is assured, the mold is immersed into a quenching bath (step 4) to form a substantially amorphous atomic structure. The casting of bulk amorphous alloy is then removed from the mold to apply other post-cast finishing processes such as polishing (step 5).

The provided bulk solidifying amorphous alloy is such that, it has a critical cooling rate of less than 1,000° C./sec, so that a section having a thickness greater than 0.5 mm can be readily cast into an amorphous structure during the fabrication of dental prosthesis. However, more preferably, the critical cooling rate is less than 100° C./sec and most preferably less than 10° C./sec. In one preferred embodiment of the invention, the dental prosthesis is cast by providing a bulk-solidifying amorphous alloy having a coefficient of thermal expansion of less than about $10^{-5}$ (m/m ° C.), and a glass transition temperature of less than 400° C., and preferably less than 300° C., in order to achieve a high level of replication of the prosthesis mold features after casting.

In a preferred embodiment, the molten amorphous alloy is superheated well above the melting temperature by 100° C. or more. This will provide higher fluidity and will allow the molten alloy to flow a much longer time before solidification. This is especially preferred in cases where the dental prosthesis has a very high aspect ratio (i.e. long and skinny shapes), and/or highly intricate shapes are to be duplicated.

In another preferred embodiment, the feedstock alloy is heated to the molten state under an inert atmosphere and preferably under vacuum.

Regardless of the actual casting method used, the mold itself can be prepared by various methods and preferably by an investment-cast method. In addition, various mechanisms can be utilized to feed the molten alloy into the mold. For example, gravity-feeding methods can be readily utilized, though other mechanisms providing external pressure are preferred. Such mechanisms can use centrifugal forces and/or inert gas pressure. Finally, various configurations of alloy feeding can be utilized, such as bottom-feeding. Another feeding method comprises counter-gravity feeding and casting, in such a method the feeding method is preferably carried out with vacuum suction assistance.

Although specific embodiments are disclosed herein, it is expected that persons skilled in the art can and will design metallic dental prostheses and methods of making such devices that are within the scope of the following description either literally or under the Doctrine of Equivalents.

What is claimed is:

1. A dental prosthesis comprising a replication of at least one surface feature of at least one tooth having at least one portion formed of a bulk-solidifying amorphous alloy that is free from Ni or Al, said bulk-solidifying amorphous alloy having an elastic strain limit of about 1.2% or more, a high hardness value of at least about 4 GPa, a glass transition temperature lower than 400° C., and a coefficient of thermal expansion of about $10^{-5}$ (m/m ° C.) or less, wherein the bulk-solidifying amorphous alloy is based on ferrous metals.

2. The dental prosthesis as described in claim 1, wherein the bulk-solidifying amorphous alloy further comprises Zr, Cu and B.

3. A dental prosthesis as described in claim 1, wherein the bulk-solidifying amorphous alloy has an elastic strain limit of about 1.8% or more.

4. The dental prosthesis as described in claim 1, wherein the bulk-solidifying amorphous alloy has a high fracture toughness of at least about 10 ksi√in.

5. The dental prosthesis as described in claim 1, wherein the bulk-solidifying amorphous alloy has a high hardness value of at least 5.0 GPa.

6. The dental prosthesis 1 as claimed in claim 1, wherein the bulk-solidifying amorphous alloy further comprises a ductile metallic crystalline phase precipitate.

7. The dental prosthesis as described in claim 1, wherein the dental prosthesis is coated with a biocompatible resin cement.

8. The dental prosthesis as described in claim 7, wherein the cement is reinforced with a metal primer agent and an oxide selected from the group consisting of alumina, magnesia, zirconia, and a combination of these oxides.

9. The dental prosthesis as described in claim 1, wherein the at least one portion formed from the bulk-solidifying amorphous alloy has a section thickness of at least 0.5 mm.

10. The dental prosthesis as described in claim 1, wherein the dental prosthesis is in the form of a dental device selected from the group consisting of a crown, a bridge or a cap.

11. The dental prosthesis of claim 1, wherein the bulk-solidifying amorphous alloy comprises Be.

12. A dental prosthesis comprising a replication of at least one surface feature of at least one tooth having at least one portion formed of a bulk-solidifying amorphous alloy that is free from Ni or Al, said bulk-solidifying amorphous alloy having an elastic strain limit of about 1.2% or more, a glass transition temperature lower than 400° C., and a coefficient of thermal expansion of about $10^{-5}$ (m/m ° C.) or less, wherein the bulk-solidifying amorphous alloy has a hardness of about 7.5 GPa and higher.

13. The dental prosthesis as described in claim 12, wherein the bulk-solidifying amorphous alloy is based on ferrous metals.

14. An object comprising a replication of at least one surface feature of a near-to-net shape object on at least one portion formed of a bulk-solidifying amorphous alloy having an elastic strain limit of about 1.2% or more, a high hardness value of at least about 4 GPa, a glass transition temperature up to 450° C., and a coefficient of thermal expansion of about $10^{-5}$ (m/m ° C.) or less, wherein the bulk-solidifying amorphous alloy is based on ferrous metals.

15. The object of claim 14, wherein the bulk-solidifying amorphous alloy further comprises Zr, Ni and Cu, and optionally further comprises one or more of Be, Al, and B.

16. A object of claim 14, wherein the bulk-solidifying amorphous alloy has an elastic strain limit of about 1.8% or more.

17. The object of claim 14, wherein the bulk-solidifying amorphous alloy has a high fracture toughness of at least about 10 ksi√in.

18. The object of claim 14, wherein the bulk-solidifying amorphous alloy has a high hardness value of at least about 5.0 GPa.

19. The object of claim 14, wherein the bulk-solidifying amorphous alloy further comprises a ductile metallic crystalline phase precipitate.

20. The object of claim 14, wherein the bulk-solidifying amorphous alloy is Al, Ni or Be free.

21. The object of claim 14, wherein the bulk-solidifying amorphous alloy is Ni or Al free.

22. The object of claim 14, wherein the bulk-solidifying amorphous alloy comprises Be.

23. The object of claim 14, wherein the at least one portion formed from the bulk-solidifying amorphous alloy has a section thickness of at least 0.5 mm.

24. The object of claim 14, wherein the bulk-solidifying amorphous alloy lacks any crystal structure and the bulk-solidifying amorphous alloy is configured to replicate intricacies of an impression.

25. An object comprising a replication of at least one surface feature of a near-to-net shape object on at least one portion formed of a bulk-solidifying amorphous alloy having an elastic strain limit of about 1.2% or more, a glass transition temperature lower than 400° C., and a coefficient of thermal expansion of about $10^{-5}$ (m/m ° C.) or less, wherein the bulk-solidifying amorphous alloy has a hardness of about 7.5 GPa and higher.

26. The object of claim 25, wherein the bulk-solidifying amorphous alloy is based on ferrous metals.

* * * * *